United States Patent [19]
Park et al.

[11] Patent Number: 6,127,546
[45] Date of Patent: Oct. 3, 2000

[54] PROCESS FOR THE PREPARATION OF OXAZOLINE COMPOUND

[75] Inventors: Jin Kyu Park, Seoul; Kyung Seok Choi, Ichon; Han Won Lee, Seoul; Sung Ki Seo, Chungcheongbuk-do; Won Hun Ham; Chang Young Oh, both of Seoul; Kee Young Lee, Kyonggi-do; Yong Hyun Kim, Seoul; Min Sung Park, Masan, all of Rep. of Korea

[73] Assignee: Dong Kook Pharmaceutical Co., Ltd., Seoul, Rep. of Korea

[21] Appl. No.: 09/515,591

[22] Filed: Feb. 29, 2000

[51] Int. Cl.⁷ .................................................. C07D 263/14
[52] U.S. Cl. .............................................. 548/239
[58] Field of Search ............................................. 548/239

[56] References Cited

PUBLICATIONS

Ansari et al., J. Am. Oil Chem. Soc., (1986), 63(7), pp. 908–914, Jul. 1986.

*Primary Examiner*—Laura L. Stockton
*Attorney, Agent, or Firm*—Hickman Coleman & Hughes, LLP

[57] ABSTRACT

The present invention relates to a process for the preparation of an oxazoline compound which is easily chemically converted to a beta-amino-alpha-hydroxy acid or a gamma-amino-beta-hydroxy acid. The method comprises producing a compound of the following formula (4) using α-amino acid. The produced compound (4) is subjected to an intramolecular cyclization to produce an oxazoline compound of the following formula (3). The oxazoline compound (3) is oxidized at a vinyl group with $RuCl_3$ or $NaIO_4$ to produce an oxazoline compound of the following formula (1) which is easily chemically converted to a beta-amino-alpha-hydroxy acid. Alternatively, the oxazoline compound (3) may also be treated with 9-borabiclo[3.3.1]nonane such that a hydroxy group is introduced into the end of the vinyl group of the oxazoline compound(3). The introduced end hydroxy group is oxidized with $RuCl_3$ or $NaIO_4$ to produce an oxazoline compound of the following formula (2) which is easily chemically converted to a gamma-amino-hydroxy acid.

6 Claims, 1 Drawing Sheet

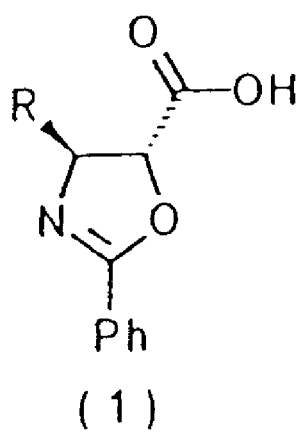
(1)
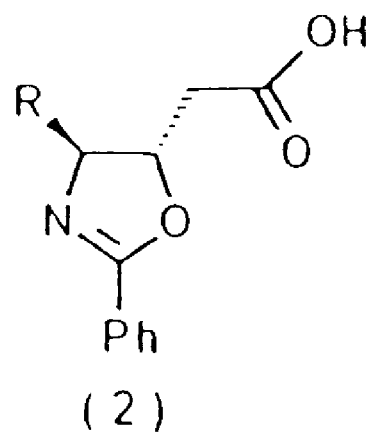
(2)
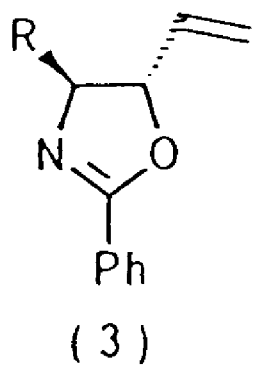
(3)
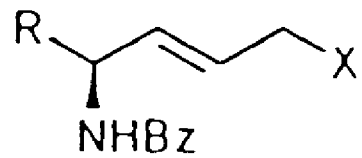
(4)

PROCESS FOR THE PREPARATION OF OXAZOLINE COMPOUND

BACKGROUND OF THE INVENTION

1. Field of the Invention

The present invention relates to a process for the preparation of an oxazoline compound which is easily chemically converted to γ-amino-α-hydroxy acid (hereinafter, called "β-a-α-h") or γ-amino-β-hydroxy acid (hereinafter, called "γ-a-β-h") exhibiting a strong pharmacological activity.

2. Description of the Prior Art

β-a-α-h and γ-a-β-h are of great interest as very useful compounds because of having a variety of pharmacological activity. Examples of these compounds include (2R, 3S)-N-benzoyl-3-phenylisoserine of the following formula I which is a side chain of Taxol useful as an anti-cancer agent, (2S,3S)-3-amino-2-hydroxy-4-phenylbutanoic acid of the following formula II which is a non-leucine moiety of bestatine exhibiting immuno-modulating, anti-cancer and anti-fungal actions, and statin of the following formula III which is ACE (an Angiotensin Converting Enzyme) inhibitor, and 4-amino-3-hydroxy-5-phenylpentanoic acid which is an analogue of statin represented by the following formula IV.

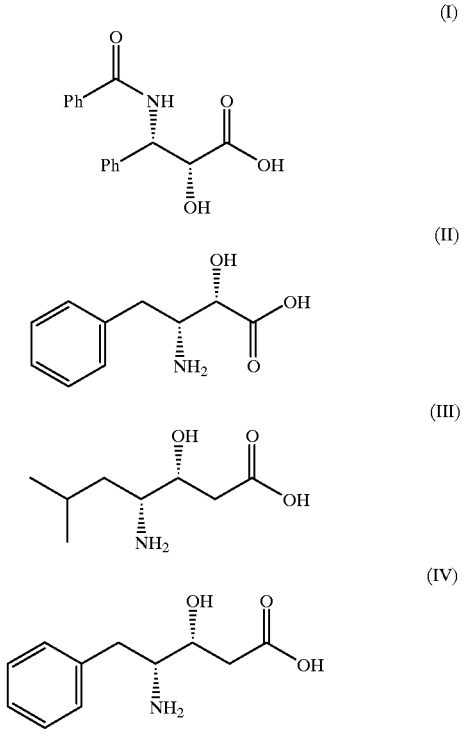

There were disclosed many processes for the preparation of β-a-α-h and γ-a-β-h. The preparation of (2R,3S)-N-benzoyl-3-phenylisoserine, which is a side chain of Taxol, was described in Tetrahedron Letters., 1994, 35, 2845–2848, 1994, 35, 9289–9292, J. Org. Chem., 1994, 59, 1238–1240, and J. Am. Chem. Soc., 1995, 117, 7824–7825. Moreover, David et al., in Tetrahedron Letters, 1994, 26, 4483–4484, has reported the preparation of an oxazoline compound which was easily chemically converted to (2R,3S)-N-benzoyl-3-phenylisoserine.

Furthermore, the preparation of (2S,3S)-3-amino-2-hydroxy-4-phenylbutanoic acid, which is a non-leucine moiety of bestatine, was disclosed in Tetrahedron Letters, 1995, 36, 909–912; Tetrahedron Letters, 1994, 35, 6123–6126; and Tetrahedron Letters, 1993, 34, 7557–7560.

Additionally, the preparations of statine represented by the above formula III, and of 4-amino-3-hydroxy-5-phenylpentanoic acid represented by the above formula IV, were described in J. Org. Chem., 1997, 62, 2292–2297; J. Org. Chem., 1995, 60, 6248–6249; U.S. Pat. No. 4,803,292; and Tetrahedron Letters, 190, 31, 7359–7362.

SUMMARY OF THE INVENTION

The present invention provides a process for the preparation of an oxazoline compound capable of being easily chemically converted to β-a-α-h or γ-a-β-h having a strong pharmacological activity. For the starting material in this process, an α-amino acid is used, such as alanine, valine, leucine, cystein, cyclohexylglycine, cyclohexylalanine, phenylglycine, p-hydroxyphenylglycine, phenylalanine, or p-hydroxyphenylalanine. Moreover, after the starting material is subjected to several reaction steps, the resulting compound is subjected to an intramolecular cyclization reaction while using a palladium compound as a catalyst to produce the oxazoline compound.

DETAILED DESCRIPTION OF THE PREFERRED EMBODIMENTS

The foregoing and other objects, features and advantages of the invention will be apparent to those skilled in the art to which the present invention relates from reading the following specification.

In accordance with the present invention, an α-amino acid, such as alanine, valine, leucine, cystein, cyclohexylglycine, cyclohexylalanine, phenylglycine, p-hydroxyphenylglycine, phenylalanine, or p-hydroxyphenylalanine, is used as the starting material to produce a compound represented by the following formula (4).

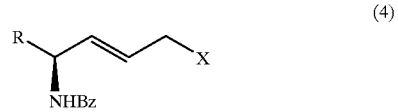

(4)

Thereafter, the compound of the formula (4) is subjected to an intramolecular cyclization reaction while using a palladium compound as a catalyst to produce an oxazoline compound represented by the following formula (3).

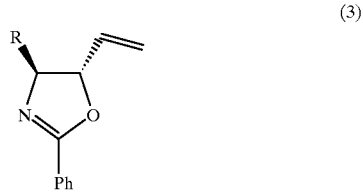

(3)

The produced oxazoline compound of the formula (3) is then oxidized at a vinyl group with RuCl₃ and NaIO₄ so as to produce an oxazoline compound of the following formula (1) which is easily chemically converted ot a beta-amino-alpha-hydroxy acid.

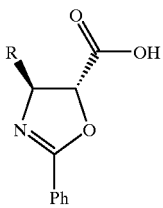

(1)

Alternatively, the produced oxazoline compound of the formula (3) is treated with 9-borabicyclo[3.3.1]nonane such that a hydroxy group is introduced into the end of a vinyl group of the oxazoline compound (3). The introduced end hydroxy end group is then oxidized with RuCl₃ and NaIO₄ so as to produce an oxazoline compound of the following formula (2) which is easily chemically converted into a gamma-amino-alpha-hydroxy acid.

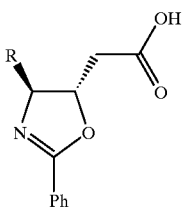

(2)

The process of the present invention is composed of the preparation of a compound of the formula (4) capable of reacting with palladium using α-amino acid as the starting material, and the preparation of the oxazoline compound of the formula (1) or (2) by an intramolecular cyclization reaction of the compound (4) using a palladium compound as a catalyst.

The preparation of a compound of the formula (4) capable of reacting with palladium is carried out as indicated in the following reaction scheme I:

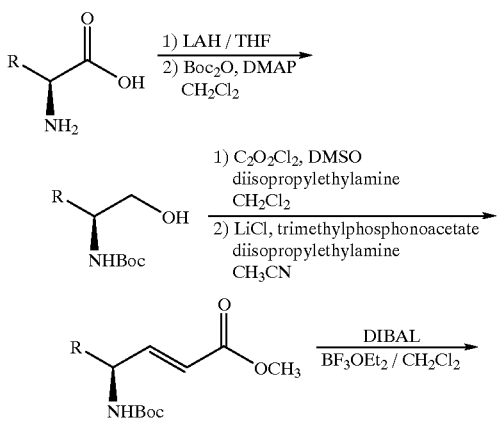

-continued

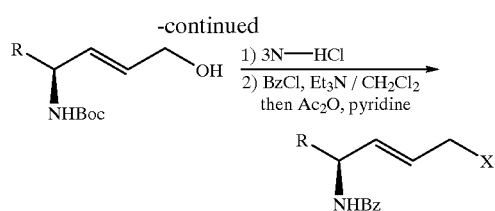

where R is methyl, isopropyl, isobutyl, sec-butyl, thiomethyl, cyclohexyl, cyclohexylmethyl, phenyl, p-hydroxyphenyl, phenylmethyl, or p-hydroxyphenylmethyl, LAH is lithium aluminum hydride (Li(AlH₄)), THF is tetrahydrofuran, DMSO is dimethylsulfoxide, DMAP is dimethylaminopyridine, DIBAL is diisobutylaluminum hydride, Bz is benzoyl, and X is acetate, benzoate, or carbonate, or halide such as Cl, Br, or I.

The preparation of the oxazoline compound of the formula (4) will be described with reference to the reaction scheme I.

For the preparation of the compound of the formula (4), 2.0 to 3.0 equivalents of α-amino acid are stirred at a temperature of 60 to 100° C. for 6 to 10 hours to give amino alcohol to which 1.0 to 1.5 equivalents of di-tert-butyl bicarbonate is then added. The resulting mixture is stirred at a temperature of 40 to 60° C. for 6 to 10 hours to obtain N-tert-butyloxycarbonyl amino alcohol.

Then, the obtained N-tert-butyloxycarbonyl amino alcohol is reacted with 1.0 to 2.0 equivalents of oxalyl chloride, 1.1 to 2.1 equivalents of dimethylsulfoxide, and 4.0 to 8.0 equivalents of diisopropylethylamine at a temperature of −78° C. for one hour to obtain aldehyde. Next, the obtained aldehyde is reacted with 1.0 to 1.5 equivalents of lithium chloride, 1.0 to 1.5 equivalents of trimethylphosphonoacetate, and 1.0 to 1.5 equivalents of diisopropylethylamine for 1 to 24 hours in the presence of an anhydrous acetonitrile solvent to produce α,β-unsaturated ester.

Following this, the produced a, -unsaturated ester is reacted with 1.0 to 1.5 equivalents of boron trifluoride-diethyl etherate and 3.0 to 4.0 equivalents of diisobutylaluminium at a temperature of −60 to −78° C. for 30 minutes to 2 hours to produce allyl alcohol.

Then, the produced allyl alcohol is reacted with a solution of 2N to 4N HCl in ethyl acetate at room temperature for 1 to 3 hours, followed by reacting with 0.95 to 1.05 equivalents of benzoyl chloride, to produce N-benzoyl allyl alcohol. Further, allyl alcohol in the produced N-benzoyl allyl alcohol is converted to a leaving group indicated by the symbol X in the reaction scheme I.

As the leaving agent, acetate, benzoate, carbonate, or halide is used. The acetate, benzoate, or carbonate is prepared with 1.0 to 1.2 equivalents of acetic anhydride, benzoyl chloride, or methyl chloroformate, respectively. The halide is prepared with 1.0 to 2.0 equivalents of methane sulfonyl halide, 0.1 to 0.5 equivalents of dimethylaminopyridine, and 1.0 to 2.0 equivalents of triethylamine.

The preparation of the oxazoline compound of the formula (1) or (2) is carried out as indicated in the following reaction scheme II:

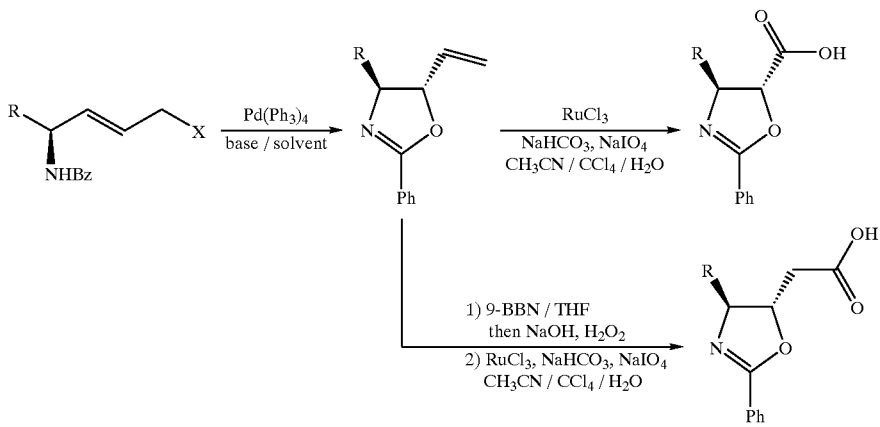

where R is methyl, isopropyl, isobutyl, sec-butyl, thiomethyl, cyclohexyl, cyclohexylmethyl, phenyl, p-hydroxyphenyl, phenylmethyl, or p-hydroxyphenylmethyl, 9-BBN is 9-borabicyclo[3.3.1]nonane, THF is tetrahydrofuran, Pd(Ph$_3$)$_4$ is tetrakistriphenylphosphine palladium, and X is acetate, benzoate, or carbonate, or halide such as Cl, Br, or I.

The preparation of the oxazoline compound of the formula (1) or (2) will be described with reference to the reaction scheme II.

A base useful for the preparation of the oxazoline compound of the formula (3) from the compound of the formula (4) is 1.0 to 2.0 equivalents of sodium hydride, or 2.0 to 3.0 equivalents of calcium carbonate. If sodium hydride is used as the base, the compound of the formula (4) is then stirred in methylene chloride as a solvent at a temperature of 30 to 40° C. for 24 to 48 hours to obtain the compound of the formula (3). On the other hand, if calcium hydride is used as a base, the compound of the formula (4) is then stirred in acetonitrile as a solvent at a temperature of 80 to 120° C. for 2 to 12 hours to obtain the compound of the formula (3).

For the preparation of the compound of the formula (2) from the compound of the formula (3), the compound of the formula (3) is stirred together with 0.02 to 0.2 equivalents of ruthenium chloride, 4.5 to 8.5 equivalents of sodium bicarbonate, and 4.5 to 6.5 equivalents of sodium periodate at room temperature for 24 to 72 hours. A solvent used in the stirring is a mixed solvent of acetonitrile/carbon tetrachloride/water=1:1:1 to 2:2:3 (v/v), and used in the amount of 1 to 20 ml relative to one mmol of the compound of the formula (3).

Meanwhile, the preparation of the compound of the formula (1) from the compound of the formula (3) is composed of a hydroboration and then an oxidation. For the hydroboration, after the compound of the formula (3) is reacted with 2 to 6 equivalents of 9-BBN at room temperature for 12 to 36 hours, the resulting compound is treated with ethyl alcohol, 6N NaOH, or H$_2$O$_2$ to obtain a primary alcohol. The obtained alcohol is then oxidized to produce the compound of the formula (1) For the oxidation, the obtained alcohol is stirred together with 0.02 to 0.16 equivalents of ruthenium chloride, 4.5 to 8.5 equivalents of sodium bicarbonate, and 4.5 to 6.5 equivalents of sodium periodate at room temperature for 12 to 24 hours. A solvent used in the stirring is a mixed solvent of acetonitrile/carbon tetrachloride/water=1:1:1 to 2:2:3 (v/v), and used in the amount of 1 to 20 ml relative to one mmol of the compound of the formula (3).

Even though the palladium compound used as a catalyst in the present invention is indicated above to be tetrakistriphenylphosphine palladium, it is also possible to use a compound having, as a ligand, tributylphosphine palladium, tri-o-tolylphosphine palladium, tri-p-tolylphosphine palladium, or tris(dibenzylidene)dipalladium.

Moreover, although a mixture of palladium acetate (Pd(OAc)$_2$) or palladium chloride (PdCl$_2$) with triphenylphosphine (Ph$_3$P) may also used as a catalyst while resulting in an excellent reactivity, it is most preferable to use tetrakistriphenylphosphine palladium as a catalyst.

The present invention will be further described with reference to the following examples. Note, however, that the examples are included herein for only explanation purpose and they are not restrictive of the present invention.

EXAMPLE 1

Synthesis of N-tert-butyloxy-carbonylphenylglycinol 4.55 g (120 mmol) of lithium aluminum hydride (Li(AlH$_4$) was suspended in 210 ml of tetrahydrofuran to which 9.07 g (60 mmol) of (S)-(+)-phenylglycine was then slowly added. After adding (S)-(+)-phenylglycine, the mixture was heated to reflux at 90° C. for 6 hours, cooled to room temperature, added with 7.3 ml of 10% aqueous sodium hydroxide solution and 9.1 ml of H$_2$O in sequence, and then stirred for 5 minutes.

At the end of the stirring, a solution of 14.40 g (66 mmol) of di-tert-butyl bicarbonate and 200 mg (1.64 mmol) of dimethyl aminopyridine in 80 ml of methylene chloride was added. The mixture was heated to reflux at 90° C. for 6 hours, cooled to room temperature, filtered through a sodium sulfate (Na$_2$SO$_4$) pad, and then washed with methylene chloride four times.

Following the washing, an organic layer was concentrated under reduced pressure, and then recrystallized from cyclohexane, thereby obtaining 10.49 g (74% yield) of N-tert-butyloxy-carbonylphenylglycinol.

$^1$H N(CDCl$_3$) δ 1.43(s, 9H), 3.82(br s, 2H), 4.77(br s, 1H), 5.31(br s, 1H), 7.26–7.38(m, 5H);

$^{13}$C NMR (CDCL$_3$) δ 22.1, 57.6, 67.6, 80.7, 127.3, 128.4, 129.5, 140.1, 156.8

EXAMPLE 2

Synthesis of N-tert-butyloxycarbonylphenylalaninol 4.55 g (120 mmol) of lithium aluminum hydride (Li(AlH$_4$) was suspended in 210 ml of tetrahydrofuran to which 9.91 g (60 mmol) of (S)-(+)-phenylalanine was then carefully added. After adding (S)-(+)-phenylalanine, the mixture was heated to reflux at 90° C. for 6 hours, cooled to room temperature, added with 7.3 ml of 10% aqueous sodium hydroxide solution and 9.1 ml of $H_2O$ in sequence, and then stirred for 5 minutes.

At the end of the stirring, a solution of 14.40 g (66 mmol) of di-tert-butyl bicarbonate and 200 mg (1.64 mmol) of dimethyl aminopyridine in 80 ml of methylene chloride was added. The mixture was heated to reflux at 70° C. for 6 hours, cooled to room temperature, filtered through a sodium sulfate ($Na_2SO_4$) pad, and then washed with methylene chloride four times.

Following the washing, an organic layer was concentrated under reduced pressure, and then recrystallized from methylene chloride-cyclohexane, thereby obtaining 11.31 g (75% yield) of N-tert-butyloxy-carbonylphenylalaninol.

$^1$H NMR (CDCl$_3$) δ 1.39(s, 9H), 2.85(d, J=7.2 Hz, 2H), 3.56(dd, J=10.8 Hz, J=5.4 Hz, 1H), 3.67 (dd, J=10.8 Hz, J=3.6 Hz, 1H), 3.88(m, 1H), 4.86(br s, 1H), 7.22–7.34(m, 5H);

$^{13}$C NMR (CDCL$_3$) δ 28.3, 37.5, 53.7, 64.2, 79.7, 126.5, 128.5, 129.3, 137.8, 156.1

EXAMPLE 3

Synthesis of N-tert-butylcarbonylleucinol 4.55 g (120 mmol) of lithium aluminum hydride (Li(AlH$_4$) was suspended in 210 ml of tetrahydrofuran to which 7.87 g (60 mmol) of (S)-(+)-leucine was then carefully added. After adding (S)-(+)-leucine, the mixture was heated to reflux at 90° C. for 6 hours, cooled to room temperature, added with 7.3 ml of 10% aqueous sodium hydride solution and 9.1 ml of $H_2O$ in sequence, and then stirred for 5 minutes.

At the end of the stirring, a solution of 14.40 g (66 mmol) of di-tert-butyl bicarbonate and 200 mg (1.64 mmol) of dimethyl aminopyridine in 80 ml of methylene chloride was added. The mixture was heated to reflux at 70° C. for 6 hours, cooled to room temperature, filtered through a sodium sulfate ($Na_2SO_4$) pad, and then washed with methylene chloride four times.

Following the washing, an organic layer was concentrated under reduced pressure, and then purified by column chromatography (hexane:ethyl acetate=3:1), thereby obtaining 8.74 g (67% yield) of N-tert-butyloxy-carbonylphenylglycinol.

$^1$H NMR (CDCl$_3$) δ 0.39(dd, 6H), 1.31(m, 2H), 1.45(s, 9H), 1.664(m, 1H), 2.56(br s, 1H), 3.50(dd, J=10.5 Hz, J=6.0 Hz, 1H), δ 3.66(d, J=10.5 Hz, 1H), 3.72(m, 1H), 4.58(br s, 1H);

$^{13}$C NMR (CDCL$_3$) δ 22.9, 23.7, 25.5, 29.1, 41.3, 51.7, 67.2, 80.3, 157.2

EXAMPLE 4

Synthesis of 2-N-(tert-butyloxycarbonyl)-amino-3-cyclohexyl-1-propanol 2 g (10.3 mmol) of (S)-2-amino-3-cyclohexyl-1-propanol, 2.26 g (10.3 mmol) of sodium hydrogen carbonate (NaHCO$_3$), and 2.6 g (31 mmol) of di-tert-butyl bicarbonate were suspended in 50 ml of methanol. The mixture was stirred at room temperature for 8 hours.

At the end of the reaction, the product was filtered, concentrated under reduced pressure to remove methanol, a solvent. Next, the concentrate was diluted with 30 ml of diethyl ether, and then further filtered. Following the filtration, an organic layer was concentrated under reduced pressure, and then purified by column chromatography (hexane:ethyl acetate=1:1), thereby obtaining 2.42 g (91% yield) of 2-N-(tert-butyloxycarbonyl)-amino-3-cyclohexyl-1-propanol.

$^1$H NMR (CDCl$_3$) δ 0.84–0.96(m, 2H), 1.12–1.28(m, 8H), 1.64(s, 9H), 1.75(m, 2H), 1.78(d, 1H), 3.49(dd, J=10.5 Hz, J=6.5 Hz, 1H), 3.66(d, J=10.5 Hz, 1H), 3.74(m, 1H), 4.57(br s, 1H);

$^{13}$C NMR (CDCL$_3$) δ 26.8, 27.0, 27.2, 29.0, 33.6, 34.4, 34.9, 39.8, 51.0, 67.4, 80.3, 157.3

EXAMPLE 5

Synthesis of methyl 4-(N-tert-butyloxycarbonyl)-amino-4-phenyl-2-butenoate 1.05 ml (12.0 mmol) of oxalyl chloride was added to 20 ml of methylene chloride. The mixture is cooled to a temperature of −78° C., and then added with 0.91 ml (12.8 mmol) of dimethylsulfoxide. Next, after the resulting mixture was stirred at −78° C. for 5 minutes, the reaction temperature was elevated to −60° C., and a suspension of 1.88 g (7.8 mmol) of N-tert-butyloxycarbonyphenylglycinol in 25 ml of methylene chloride-dimethylsulfoxide (24:1) was then added.

After the reaction temperature was elevated to −35° C., the mixture was stirred for 10 minutes, added dropwise with 8.36 ml (48.0 mmol) of diisopropylethylamine for 5 minutes, and then further stirred for 10 minutes. After the reaction temperature was elevated to room temperature, 40 ml of $H_2O$ was added. Next, an organic layer was isolated, washed with 20 ml of 1N HCl, and then with 20 ml of brine, dried with magnesium sulfate (MgSO$_4$), filtered, concentrated under reduced pressure, and then used in the subsequent reaction without purification.

397 mg (9.4 mmol) of lithium chloride was suspended in 100 ml of anhydrous acetonitrile. To this suspension, 1.5 ml (9.4 mmol) of trimethylphosphonoacetate, 1.36 ml (7.8 mmol) of diisopropylethylamine, and aldehyde prepared as described above, were sequentially added, and then stirred for 24 hours.

At the end of the stirring, the resulting material was added with 100 ml of $H_2O$, extracted with 50 ml of ethyl acetate twice, washed with 50 ml of 1H HCl twice, and then with 50 ml of brine twice, dried with MgSO$_4$, filtered, and then concentrated under reduced pressure. The concentrate was recrystallized from diethyl ether-petroleum ether, thereby obtaining 1.83 g (83%) of methyl 4-(N-tert-butyloxycarbonyl)-amino-4-phenyl-2-butenoate.

$^1$H NMR (CDCl$_3$) δ 1.44(s, 9H), 3.75(s, 3H), 4.97(br s, 1H), 5.44(br s, 1H), 5.99(dd, J=15.5 Hz, J=1.5 Hz, 1H), 7.07(dd, J=15.5 Hz, J=5.0 Hz, 1H), 7.25–7.37(m, 5H);

$^{13}$C NMR (CDCL$_3$) δ 29.0, 52.4, 56.2, 80.9, 121.8, 127.9, 128.9, 129.7, 139.9, 148.1, 155.5, 167.3

EXAMPLE 6

Synthesis of methyl 4-(N-tert-butyloxycarbonyl) amino-5-phenyl-2-pentenoate 1.05 ml (12.0 mmol) of oxalyl chloride was added to 20 ml of methylene chloride. The mixture is cooled to a temperature of −78° C., and then added with 0.91 ml (12.8 mmol) of dimethylsulfoxide. Next, after the resulting mixture was stirred at −78° C. for 5 minutes, the reaction temperature was elevated to −60° C., and a suspension of 1.96 g (7.8 mmol) of N-tert-butyloxycarbonyphenylalaniol in 25 ml of methylene chloride-dimethylsulfoxide (24:1) was then added.

After the reaction temperature was elevated to −35° C., the mixture was stirred for 10 minutes, added dropwise with 8.36 ml (48.0 mmol) of diisopropylethylamine for 5 minutes, and then further stirred for 10 minutes. After the reaction temperature was elevated to room temperature, 40 ml of $H_2O$ was added. Next, an organic layer was isolated, washed with 20 ml of 1N HCl, and then with 20 ml of brine, dried with magnesium sulfate ($MgSO_4$), filtered, concentrated under reduced pressure, and then used in the subsequent reaction without purification.

397 mg (9.4 mmol) of lithium chloride was suspended in 100 ml of anhydrous acetonitrile. To this suspension, 1.5 ml (9.4 mmol) of trimethylphosphonoacetate, 1.36 ml (7.8 mmol) of diisopropylethylamine, and aldehyde prepared as described above, were sequentially added, and then stirred for 24 hours.

At the end of the stirring, the resulting material was added with 100 ml of $H_2O$, extracted with 50 ml of ethyl acetate twice, washed with 50 ml of 1H HCl twice, and then with 50 ml of brine twice, dried with $MgSO_4$, filtered, and then concentrated under reduced pressure. The concentrate was recrystallized from diethyl ether-petroleum ether, thereby obtaining 2.07 g (87% yield) of methyl 4-(N-tert-butyloxycarbonyl)amino-5-phenyl-2-pentenoate.

$^1H$ NMR ($CDCl_3$) δ 1.40(s, 9H), 2.89(d, J=6.3 Hz, 2H), 3.72(s, 3H), 4.56(m, 2H), 5.86(dd, J=15.6 Hz, J=1.5 Hz, 1H), 6.91(dd, J=15.6 Hz, J=5.1 Hz, 1H), 7.16–7.33(m, 5H);

$^{13}C$ NMR ($CDCL_3$) δ 28.3, 40.8, 51.6, 53.7, 80.0, 120.7, 126.9, 128.6, 129.4, 136.3, 147.9, 154.9, 166.6

EXAMPLE 7

Synthesis of methyl 4-(N-tert-butyloxycarbonyl)-amino-6-methyl-2-heptenoate 1.05 ml (12.0 mmol) of oxalyl chloride was added to 20 ml of methylene chloride. The mixture is cooled to a temperature of −78° C., and then added with 0.91 ml (12.8 mmol) of dimethylsulfoxide. Next, after the resulting mixture was stirred at −78° C. for 5 minutes, the reaction temperature was elevated to −60° C., and a suspension of 1.70 g (7.8 mmol) of N-tert-butyloxycarbony-leucinol in 25 ml of methylene chloride-dimethylsulfoxide (24:1) was then added.

After the reaction temperature was elevated to −35° C., the mixture was stirred for 10 minutes, added dropwise with 8.36 ml (48.0 mmol) of diisopropylethylamine for 5 minutes, and then further stirred for 10 minutes. After the reaction temperature was elevated to room temperature, 40 ml of $H_2O$ was added. Next, an organic layer was isolated, washed with 20 ml of 1N HCl, and then with 20 ml of brine, dried with magnesium sulfate ($MgSO_4$), filtered, concentrated under reduced pressure, and then used in the subsequent reaction without purification.

397 mg (9.4 mmol) of lithium chloride was suspended in 100 ml of anhydrous acetonitrile. To this suspension, 1.5 ml (9.4 mmol) of trimethlylphosphonoacetate, 1.36 ml (7.8 mmol) of diisopropylethylamine, and aldehyde prepared as described above, were sequentially added, and then stirred for 24 hours.

At the end of the stirring, the resulting material was added with 100 ml of $H_2O$, extracted with 50 ml of ethyl acetate twice, washed with 50 ml of 1H HCl twice, and then with 50 ml of brine twice, dried with $MgSO_4$, filtered, and then concentrated under reduced pressure. The concentrate was purified by column chromatography (hexane:ethyl acetate= 8:1), thereby obtaining 1.52 g (72% yield) of methyl 4-(N-tert-butyloxycarbonyl)-amino-6-methyl-2-heptenoate.

$^1H$ NMR ($CDCl_3$) δ 0.94(dd, 6H), 1.38(m, 2H), 1.45(s, 9H), 1.69(m, 1H), 3.73(s, 3H), 4.33(m, 1H), 4.45(br s, 1H), 5.92(dd, J=15.8 Hz, J=1.5 Hz, 1H), 6.84(dd, J=15.5 Hz, J=5.5 Hz, 1H);

$^{13}C$ NMR ($CDCL_3$) δ 22.2, 22.7, 24.7, 28.3, 43.8, 49.8, 51.6, 80.3, 120.0, 149.2, 155.1, 166.8

EXAMPLE 8

Synthesis of methyl 4-(N-tert-butyloxycarbonyl)-amino-5-cyclohexyl-2-pentenoate 1.07 ml (12.0 mmol) of oxalyl chloride was added to 20 ml of methylene chloride. The mixture is cooled to a temperature of −78° C., and then added with 4.17 ml (23.5 mmol) of dimethylsulfoxide. Next, after the resulting mixture was stirred at −78° C. for 5 minutes, the reaction temperature was elevated to −60° C., and a suspension of 2.42 g (9.4 mmol) of N-tert-butyloxycarbony-2-amino-3-cyclohexyl-1-propanol in 25 ml of methylene chloride-dimethylsulfoxide (24:1) was then added dropwise in a state where the suspension was dissolved in 10 ml of methylene chloride.

After the reaction temperature was elevated to −35° C., the mixture was stirred for 10 minutes, added with 6.56 ml (47.0 mmol) of diisopropylethylamine for 5 minutes dropwise, and then further stirred for 10 minutes. After the reaction temperature was elevated to room temperature, 16 ml of $H_2O$ was added. Next, an organic layer was isolated, washed with 20 ml of 1N HCl, and then with 20 ml of brine, dried with magnesium sulfate ($MgSO_4$), filtered, concentrated under reduced pressure, and then used in the subsequent reaction without purification.

478 mg (11.2 mmol) of lithium chloride and 1.83 ml (11.2 mmol) of trimethylphosphonoacetate was suspended in 50 ml of anhydrous acetonitrile. To this suspension, 1.41 ml (9.4 mmol) of 1,8-diazabicyclo[5,4,0]undec-7-ene and aldehyde prepared as described above and dissolved in 20 ml of acetonitrile, were sequentially added, and then stirred for 24 hours.

At the end of the stirring, the resulting material was added with 20 ml of $H_2O$, extracted with 50 ml of ethyl acetate twice, washed with 20 ml of 1H HCl twice, and then with 50 ml of brine twice, dried with $MgSO_4$, filtered, and then concentrated under reduced pressure. The concentrate was purified by column chromatography (hexane:ethyl acetate= 8:1), thereby obtaining 2.04 g (70% yield) of methyl 4-(N-tert-butyloxycarbonyl)-amino-5-cyclohexyl-2-pentenoate.

$^1H$ NMR ($CDCl_3$) δ 0.90–0.96(m, 2H), 1.15–1.28(m, 8H), 1.64(s, 9H), 1.71(m, 1H), 1.78(d, 1H), 3.74(s, 3H), 4.37(br s, 1H), 4.43(br s, 1H), 5.92(dd, J=15.5 Hz, J=1.5 Hz, 1H), 6.84(dd, J=15.5 Hz, J=5.0 Hz, 1H);

$^{13}C$ NMR ($CDCL_3$) δ 26.0, 26.1, 26.4, 28.3, 32.4, 32.9, 33.4, 42.4, 51.5, 51.8, 77.4, 119.9, 149.3, 152.1, 166.8

EXAMPLE 9

Synthesis of 4-(N-tert-butyloxycarbonyl)amino-4-phenyl-2-butene-1-ol 29.1 g (100 mmol) of methyl 4-(N-tert-butyloxycarbonyl) amino-4-phenyl-2-butenoate was added to 200 ml of methylene chloride. The mixture is cooled to a temperature of −78° C., and then added with 13.5 ml (100 mmol) of boron trifluoride-diethyl etherate dropwise. Next, the resulting mixture was stirred at −78° C. for 30 minutes, then added with a solution of 200 ml (300 mmol) of diisobutylaluminum hydride in 1.5 mol of toluene. After stirring for 1 hour, the stirred mixture was added with a solution of 5M acetic acid in 230 ml of methylene chloride dropwise. Then, the reaction temperature was elevated to room temperature, and 500 ml of an aqueous solution of 3M tartaric acid was added. Following this, an organic layer was isolated, a water layer was washed with 200 ml of methylene chloride, and then combined with the organic layer. Then, the resulting organic layer was washed with 500 ml of a saturated aqueous solution of sodium bicarbonate, and then with 500 ml of brine, dried with magnesium sulfate ($MgSO_4$), filtered, and concentrated under reduced pressure. The concentrate was recrystallized from ether-petroleum ether, thereby obtaining 23.4 g (89% yield) of 4-(N-tert-butyloxycarbonyl)-amino-4-phenyl-2-butene-1-ol.

$^1$H NMR ($CDCl_3$) δ 1.44(s, 9H), 4.19(dd, J=5.0 H, J=1.0 Hz, 2H), 4.90(br s, 1H), 5.30(br s, 1H), 5.81(dt, J=15.5 Hz, J=5.0 Hz, 1H), 5.88(dd, J=15.5 Hz, J=5.5 Hz, 1H), 7.23–7.36(m, 5H);

$^{13}$C NMR ($CDCL_3$) δ 29.1, 56.5, 63.6, 80.5, 127.6, 128.3, 129.4, 131.1, 132.0, 142.0, 155.7

EXAMPLE 10

Synthesis of 4-(N-tert-butyloxycarbonyl)amino-5-phenyl-2-pentene-1-ol 30.5 g (100 mmol) of methyl 4-(N-tert-butyloxycarbonyl)amino-5-phenyl-2-pentenoate was added to 200 ml of methylene chloride. The mixture is cooled to a temperature of −78° C., and then added with 13.5 ml (100 mmol) of boron trifluoride-diethyl etherate dropwise. Next, the resulting mixture was stirred at −78° C. for 30 minutes, then added with a solution of 200 ml (300 mmol) of diisobutylaluminum hydride in 1.5 mol of toluene. After stirring for 1 hour, the stirred mixture was added with a solution of 5M acetic acid in 230 ml of methylene chloride dropwise. Then, the reaction temperature was elevated to room temperature, and 500 ml of an aqueous solution of 3M tartaric acid was added. Following this, an organic layer was isolated, a water layer was washed with 200 ml of methylene chloride, and then combined with the organic layer. Then, the resulting organic layer was washed with 500 ml of a saturated aqueous solution of sodium bicarbonate, and then with 500 ml of brine, dried with magnesium sulfate ($MgSO_4$), filtered, and concentrated under reduced pressure. The concentrate was recrystallized from ether-petroleum ether, thereby obtaining 25.5 g (92% yield) of 4-(N-tert-butyloxycarbonyl)-amino-5-phenyl-2-pentene-1-ol.

$^1$H NMR ($CDCl_3$) δ 1.39(s, 9H), 2.83(d, J=6.9 Hz, 2H), 4.09(br s, 1H), 4.41(br s, 1H), 4.54(br s, 1H),5.69(m, 2H), 7.16–7.32(m, 5H);

$^{13}$C NMR ($CDCL_3$) δ 28.3, 41.6, 56.0, 62.7, 79.5, 126.4, 128.3, 129.5 129.7, 131.4, 137.3, 155.2

EXAMPLE 11

Synthesis of 4-(N-tert-butyloxycarbonyl)amino-6-methyl-2-heptene-1-ol 27.1 g (100 mmol) of methyl 4-(N-tert-butyloxycarbonyl)amino-6-methyl-2-heptenoate was added to 200 ml of methylene chloride. The mixture is cooled to a temperature of −78° C., and then added with 13.5 ml (100 mmol) of boron trifluoride-diethyl etherate dropwise. Next, the resulting mixture was stirred at −78° C. for 30 minutes, then added with a solution of 200 ml (300 mmol) of diisobutylaluminum hydride in 1.5 mol of toluene. After stirring for 1 hour, the stirred mixture was added with a solution of 5M acetic acid in 230 ml of methylene chloride dropwise. Then, the solution was elevated to room temperature, and 500 ml of an aqueous solution of 3M tartaric acid was added. Following this, an organic layer was isolated, a water layer was washed with 200 ml of methylene chloride, and then combined with the organic layer. Then, the resulting organic layer was washed with 500 ml of a saturated aqueous solution of sodium bicarbonate, and then with 500 ml of brine, dried with magnesium sulfate ($MgSO_4$), filtered, and concentrated under reduced pressure. The concentrate was purified by column chromatography (hexane:ethyl acetate=2:1), thereby obtaining 20.4 g (84% yield) of 4-(N-tert-butyloxycarbonyl)amino-6-methyl-2-heptene-1-ol.

$^1$H NMR ($CDCl_3$) δ 0.89(dd, 6H), 1.30(m, 2H), 1.41(s, 9H), 1.61(m, 1H), 4.11(t, 3H), 4.38(br s, 1H), 5.55–5.60(m, 1H), 5.71–5.77(m, 1H);

$^{13}$C NMR ($CDCL_3$) δ 22.4, 22.7, 24.7 28.4, 44.7, 50.1, 63.1, 79.7 129.0, 133.0, 155.3

EXAMPLE 12

Synthesis of 4-(N-tert-butyloxycarbonyl)amino-5-cyclohexyl-2-pentene-1-ol 2.04 g (6.5 mmol) of methyl 4-(N-tert-butyloxycarbonyl)amino-5-cyclohexyl-2-pentenoate was added to 200 ml of methylene chloride. The mixture is cooled to a temperature of −78° C., and then added with 0.88 ml (7.1 mmol) of boron trifluoride-diethyl etherate dropwise. Next, the resulting mixture was stirred at −78° C. for 30 minutes, then added with a solution of 13.0 ml (19.5 mmol) of diisobutylaluminum hydride in 1.5 mol of toluene. After stirring for 1 hour, the stirred mixture was added with a solution of 5M acetic acid in 14 ml of methylene chloride dropwise. Then, the reaction temperature was elevated to room temperature, and 55 ml of an aqueous solution of 3M tartaric acid was added. Following this, an organic layer was isolated, a water layer was washed with 60 ml of methylene chloride, and then combined with the organic layer. Then, the resulting organic layer was washed with 50 ml of a saturated aqueous solution of sodium bicarbonate, and then with 50 ml of brine, dried with magnesium sulfate ($MgSO_4$), filtered, and concentrated under reduced pressure. The concentrate was purified by column chromatography (hexane:ethyl acetate=2:1), thereby obtaining 1.59 g (86% yield) of 4-(N-tert-butyloxycarbonyl)amino-5-cyclohexyl-2-pentene-1-ol.

$^1$H NMR ($CDCl_3$) δ 0.87(m, 2H), 1.14–1.31(m, 8H), 1.41(s, 9H), 1.63(m, 2H), 1.71(d, 1H), 4.11(br s, 1H), 4.14(br s, 1H), 4.18(br s, 1H), 5.59–5.61(m, 1H), 5.70–5.76 (m, 1H);

$^{13}$C NMR ($CDCL_3$) δ 26.1, 26.2, 26.4, 28.4, 33.0, 33.4, 34.1, 43.3, 49.2, 63.1, 77.4, 128.8, 133.1, 153.0

EXAMPLE 13

Synthesis of 4-(N-benzoyl)amino-4-phenyl-1-acetoxy-2-butene 2.6 g (10 mmol) of 4-(N-tert-butyloxycarbonyl)amino-4-phenyl-2-butene-1-ol was added to a solution of 10 ml of 3N-HCl in ethyl acetate, and the mixture was stirred for 30 minutes. After adding 20 ml of $H_2O$, the mixture was extracted with 30 ml of ethyl acetate. Then, a water layer was basified with potassium carbonate, extracted with 20 ml of methylene chloride twice, dried with MgSO$_4$, filtered, and concentrated under reduced pressure, thereby obtaining 1.17 g (72% yield) of 4-amino-4-phenyl-2-butene-1-ol. Next, the product was added with 20 ml of methylene chloride, cooled to 0° C., and then added with 0.83 ml (7.17 mmol) of benzoyl chloride and 1.0 ml (7.17 mmol) of triethyl amine. After stirring for 1 hour, the mixture was added with 0.68 ml (7.17 mmol) of acetic anhydride and 0.58 ml (7.58 ml) of pyridine, and then further stirred for 24 hours. After the stirred solution was added with 20 ml of H$_2$O, an organic layer was isolated, washed with 20 ml of 1N-HCl, 20 ml of a saturated aqueous solution of sodium carbonate, and then with 20 ml of brine, filtered, and then concentrated under reduced pressure. The concentrate was recrystallized from methylene chloride-hexane, thereby obtaining 2.17 g (98%) of 4-(N-benzoyl)amino-4-phenyl-1-acetoxy-2-butene.

$^1$H NMR (CDCl$_3$) δ 2.08(s, 3H), 4.63(dt, J=4.5 Hz, J=1.5 Hz, 2H), 5.82 (dt, J=15.5 Hz, J=6.0 Hz, 2H)5.89(dd, J=8.0 Hz, J=5.5 Hz, 1H), 6.06(dd, J=15.5 Hz, J=5.5 Hz, 1H) 6.37(d, J=8.0 Hz, 1H), 7.31–7.54(m, 8H), 7.79–7.81(m, 2H);

$^{13}$C NMR (CDCL$_3$) δ 21.6, 55.2, 64.8, 126.8, 127.7, 127.9, 128.6, 129.3, 129.6, 132.4, 134.1, 134.9, 141.0, 167.1, 171.4

EXAMPLE 14

Synthesis of 4-(N-benzoyl)amino-5-phenyl-1-acetoxy-2-pentene 2.77 g (10 mmol) of 4-(N-tert-butyloxycarbonyl)amino-5-phenyl-2-pentene-1-ol was added to a solution of 10 ml of 3N-HCl in ethyl acetate, and the mixture was stirred for 30 minutes. After adding 20 ml of H$_2$O, the mixture was extracted with 30 ml of ethyl acetate. Then, a water layer was basified with potassium carbonate, extracted with 20 ml of methylene chloride twice, dried with MgSO$_4$, filtered, and concentrated under reduced pressure, thereby obtaining 1.35 g (76% yield) of 4-amino-5-phenyl-2-pentene-1-ol. Next, the product was added with 20 ml of methylene chloride, cooled to 0° C., and then added with 0.88 ml (7.62 mmol) of benzoyl chloride and 1.06 ml (7.62 mmol) of triethyl amine. After stirring for 1 hour, the mixture was added with 0.72 ml (7.62 mmol) of acetic anhydride and 0.62 ml (7.62 ml) of pyridine, and then further stirred for 24 hours. After the stirred solution was added with 20 ml of H$_2$O, an organic layer was isolated, washed with 20 ml of 1N-HCl, 20 ml of a saturated aqueous solution of sodium carbonate, and then with 20 ml of brine, filtered, and then concentrated under reduced pressure. The concentrate was recrystallized from methylene chloride-hexane, thereby obtaining 2.43 g (99%) of 4-(N-benzoyl)amino-5-phenyl-1-acetoxy-2-pentene.

$^1$H NMR (CDCl$_3$) δ 2.05(s, 3H), 3.01(dd, J=6.5 Hz, J=1.5 Hz, 2H), 4.54(d, J=6.0 Hz, 2H), 5.02(m, 1H), 5.71(dd, J=15.5 Hz, J=1.5 Hz, 1H), 5.84 (dd, J=15.5 Hz, J=5.5 Hz, 1H), 6.11(d, J=8.0 Hz, 1H), 7.22–7.49(m, 8H), 7.68–7.69(m, 2H);

$^{13}$C NMR (CDCL$_3$) δ 20.9, 41.0 51.3, 64.1, 117.9, 125.1, 126.8, 128.5, 128.6, 129.5, 131.5, 133.8, 134.4, 136.8, 166.7, 170.6

EXAMPLE 15

Synthesis of 4-(N-benzoyl)amino-6-methyl-1-acetoxy-2-heptene 2.4 g (10 mmol) of 4-(N-tert-butyloxycarbonyl)amino-6-methyl-2-heptene-1-ol was added to a solution of 10 ml of 3N-HCl in ethyl acetate, and the mixture was stirred for 30 minutes. After adding 20 ml of H$_2$O, the mixture was extracted with 30 ml of ethyl acetate. Then, a water layer was basified with potassium carbonate, extracted with 20 ml of methylene chloride twice, dried with MgSO$_4$, filtered, and concentrated under reduced pressure, thereby obtaining 1.07 g (75% yield) of 4-amino-6-methyl-2-heptene-1-ol. Next, the product was added with 20 ml of methylene chloride, cooled to 0° C., and then added with 0.83 ml (7.17 mmol) of benzoyl chloride and 1.0 ml (7.17 mmol) of triethyl amine. After stirring for 1 hour, the mixture was added with 0.68 ml (7.17 mmol) of acetic anhydride and 0.58 ml (7.17 ml) of pyridine, and then further stirred for 24 hours. After the stirred solution was added with 20 ml of H$_2$O, an organic layer was isolated, washed with 20 ml of 1N-HCl, 20 ml of a saturated aqueous solution of sodium carbonate, and then 20 ml of brine, filtered, and then concentrated under reduced pressure. The concentrate was purified by column chromatography (hexane:ethyl acetate=2:1), thereby obtaining 2.11 g (98%) of 4-(N-benzoyl)amino-6-methyl-1-acetoxy-2-heptene.

$^1$H NMR (CDCl$_3$) δ 0.97(dd, 6H), 1.50(m, 2H), 1.71(m, 1H), 2.07(s, 3H), 4.56(d, J=3.5 Hz, 2H), 4.78(m, 1H), 5.78(m, 2H), 5.96(d, J=7.5 Hz, 1H), 7.43–7.53(m, 3H), 7.77–7.79(m, 2H);

$^{13}$C NMR (CDCl$_3$) δ 20.9, 22.3, 22.8, 24.9, 44.2, 48.9, 64.3, 124.4, 126.8, 128.5, 131.5, 134.5, 135.2, 166.6, 170.6

EXAMPLE 16

Synthesis of 4-(N-benzoyl)amino-5-cyclohexyl-1-acetoxy-2-pentene 1.5 g (5.3 mmol) of 4-(N-tert-butyloxycarbonyl)amino-5-cyclohexyl-2-pentene-1-ol was added to a solution of 10 ml of 3N-HCl in ethyl acetate, and the mixture was stirred for 30 minutes. After adding 20 ml of H20, the mixture was extracted with 30 ml of ethyl acetate. Then, a water layer was basified with potassium carbonate, extracted with 20 ml of methylene chloride twice, dried with MgSO$_4$, filtered, and concentrated under reduced pressure, thereby obtaining 0.75 g (78% yield) of 4-amino-5-cyclohexyl-2-pentene-1-ol. Next, the product was added with 20 ml of methylene chloride, cooled to 0° C., and then added with 0.49 ml (4.29 mmol) of benzoyl chloride and 0.60 ml (4.29 mmol) of triethyl amine. After stirring for 1 hour, the mixture was added with 0.52 ml (6.43 mmol) of acetic anhydride and 0.81 ml (8.58 mmol) of pyridine, and then further stirred for 24 hours. After the stirred solution was added with 20 ml of H$_2$O, an organic layer was isolated, washed with 20 ml of 1N-HCl, 20 ml of a saturated aqueous solution of sodium carbonate, and then with 20 ml of brine, filtered, and then concentrated under reduced pressure. The concentrate was purified by column chromatography (hexane:ethyl acetate= 3:1), thereby obtaining 1.20 g (90% yield) of 4-(N-benzoyl)amino-5-cyclohexyl-1-acetoxy-2-pentene.

$^1$H NMR (CDCl$_3$) δ 0.87–1.02(m, 2H), 1.10–1.26(m, 4H), 1.33–1.41(m, 1H), 1.51(m, 1H), 1.72(m, 2H), 1.83(d, 1H), 2.06(s, 3H), 4.57(m, 2H), 4.80(m, 1H), 5.75(m, 2H), 5.98(m, 1H), 7.42(m, 1H), 7.51(m, 1H), 7.77(m, 1H);

$^{13}$C NMR (CDCL$_3$) δ 21.7, 26.8, 26.9, 27.1, 33.6, 34.2, 35.0, 43.5, 48.9, 65.0, 124.9, 127.5, 129.3, 132.2, 135.2, 136.1, 167.3, 171.4

EXAMPLE 17

Synthesis of (4S-trans)-4,5-dihydro-2,4-diphenyl-5-vinyloxazoline

To 927 mg (3 mmol) of 4-(N-benzoyl)amino-4-phenyl-1-acetoxy-2-butene was added 50 ml of acetonitrile, 930 mg (6 mmol) of potassium carbonate, and 172 mg (0.15 mmol) of tetrakistriphenylphosphine palladium (Pd(PPh$_3$)$_4$), in sequence. The mixture was heated to reflux at 70° C. for 24 hours, and then cooled to room temperature in air. After this, the cooled mixture was filtered through a cellite pad, concentrated under reduced pressure, purified by column chromatography (hexane:ethyl acetate=10:1), thereby obtaining 546 mg (73% yield) of (4S-trans)-4,5-dihydro-2,4-diphenyl-5-vinyloxazoline.

$^1$H NMR (CDCl$_3$) δ 4.88(dd, J=7.0, 8.0 Hz, 1H), 5.05(d, J=8.0 Hz, 1H), 5.33(d, J=10.5 Hz, 1H), 5.38(d, J=17.5 Hz, 1H), 6.09(ddd, J=7.0, 10.5, 17.5 Hz, 1H), 7.31–7.53(m, 8H), 8.08(m, 2H);

$^{13}$C NMR (CDCL$_3$) δ 76.8, 89.2, 118.6, 127.4, 128.3, 128.4, 129.1, 129.2, 129.5, 132.3, 136.6, 142.4, 164.7

EXAMPLE 18

Synthesis of (4S-trans)-4,5-dihydro-4-benzyl-2-phenyl-5-vinyl-oxazoline 120 mg (60% dispersion, 3 mmol) of sodium hydride was suspended in methylene chloride. To this suspension, a solution of 970 mg (3 mmol) of 4-(N-benzoyl)amino-5-phenyl-1-acetoxy-2-pentene in 10 ml of methylene chloride was slowly added dropwise at 0° C., followed by 172 mg (0.15 mmol) of tetrakistriphenylphosphine palladium (Pd(PPh$_3$)$_4$). The mixture was heated to reflux at 35° C. for 24 hours, and then cooled to room temperature in air. After this, the cooled mixture was filtered through a silica pad, washed with 20 ml of methylene chloride, distilled under reduced pressure, purified by column chromatography (hexane:ethyl acetate=10:1), thereby obtaining 616 mg (73% yield, 91% diastereomeric excess) of (4S-trans)-4,5-dihydro-4-benzyl-2-phenyl-5-vinyl-oxazoline.

$^1$H NMR (CDCl$_3$) δ 2.79(dd, J=7.5, 13 Hz, 1H), 3.26(dd, J=5.5, 13 Hz, 1H), 4.26(ddd, J=5.5, 7.0, 7.5 Hz, 1H), 4.76(dd, J=6.5, 7.0 Hz, 1H), 5.06(dd, 2H), 5.72(ddd, 1H), 7.22–7.51(m, 8H), 7.97–8.01(m, 2H);

$^{13}$C NMR (CDCL$_3$) δ 42.2, 74.5, 84.6, 116.5, 126.5, 128.3, 128.4, 129.2, 129.5, 131.3, 136.2, 137.5, 163.0

EXAMPLE 19

Synthesis of (4S-trans)-4,5-dihydro-4-isobutyl-2-phenyl-5-vinyl-oxazoline 120 mg (60% dispersion, 3 mmol) of sodium hydride was suspended in 30 ml of methylene chloride. To this suspension, a solution of 895 mg (3 mmol) of 4-(N-benzoyl) amino-6-methyl-1-acetoxy-2-heptene in 10 ml of methylene chloride was slowly added dropwise at 0° C., followed by 172 mg (0.15 mmol) of tetrakistriphenylphosphine palladium (Pd(PPh$_3$)$_4$). The mixture was heated to reflux for 24 hours. After this, the resulting material was filtered through a silica pad, washed with 20 ml of methylene chloride, distilled under reduced pressure, purified by column chromatography (hexane:ethyl acetate=20:1), thereby obtaining 515 mg (75% yield, 91% diastereomeric excess) of (4S-trans)-4,5-dihydro-4-isobutyl-2-phenyl-5-vinyl-oxazoline.

$^1$H NMR (CDCl$_3$) δ 0.98(dd, 6H), 1.41(m, 1H), 1.65(m, 1H), 1.89(m, 1H), 4.01(dd, J=9.5 Hz, J=7.0 Hz, 1H), 4.63 (dd, J=7.0, 1H), 5.25(d, J=10.5 Hz, 1H), 5.39(d, J=16 Hz, 1H), 5.96(ddd, J=16.0 Hz, J=10.5 Hz, J=7.0 Hz), 7.39–7.49 (m, 3H), 7.95–7.98(m, 2H);

$^{13}$C NMR (CDCL$_3$) δ 22.6, 22.9, 25.0, 45.2, 70.8, 86.3, 117.1, 128.0, 128.2, 128.3, 131.2, 136.5, 162.4

EXAMPLE 20

Synthesis of (4S-trans)-4,5-dihydro-4-cyclohexylmethyl-2-phenyl-5-vinyl-oxazoline 65 mg (60% dispersion, 2.73 mmol) of sodium hydride was suspended in 15 ml of methylene chloride. To this suspension, a solution of 900 mg (2.73 mmol) of 4-(N-benzoyl)amino-5-cyclohexyl-1-acetoxy-2-pentene in 10 ml of methylene chloride was slowly added dropwise at room temperature, followed by 312 mg (0.27 mmol) of tetrakistriphenylphosphine palladium (Pd(PPh$_3$)$_4$). The mixture was stirred at 40° C. for 24 hours. At the end of the reaction, the resulting material was filtered through a silica pad, washed with 20 ml of methylene chloride, distilled under reduced pressure, and then purified by column chromatography (hexane:ethyl acetate=20:1), thereby obtaining 528 mg (72% yield, 91% diastereomeric excess) of (4S-trans)-4,5-dihydro-4-cyclohexylmethyl-2-phenyl-5-vinyl-oxazoline.

$^1$H NMR (CDCl$_3$) δ 0.95–0.98(m, 2H), 1.21–1.28(m, 5H), 1.41–1.44(m, 1H), 1.64–1.72(m, 3H), 1.80(m, 2H), 4.04(dd, J=7.5 Hz, J=7.0 Hz, 1H), 4.62(dd, J=7.0 Hz, 1H), 5.24(d, J=10.0 Hz, 1H), 5.37(d, J=17.0 Hz, m 1H), 5.96(ddd, J=17.0 Hz, J=10.0 Hz, J=7.0 Hz), 7.38–7.48(m, 3H), 7.95–7.97(m, 2H);

$^{13}$C NMR (CDCL$_3$) δ 26.2, 26.5, 26.6, 33.3, 33.5, 34.3, 43.7, 70.1, 86.3, 117.0, 128.23, 128.25, 128.26, 131.2, 136.4, 162.4

EXAMPLE 21

Synthesis of (4S-trans)-4,5-dihydro-2,4-diphenyloxazoline-5-carboxylic Acid 30 ml of a mixed solution of acetonitrile/carbon tetrachloride/water (1:1:1) was added to 346 mg (1.5 mmol) of (4S-trans)-4,5-dihydro-2,4-diphenyl-5-vinyl-oxazoline while stirring at room temperature. The mixture was added with 819 mg (9.75 mmol) of sodium bicarbonate and 1.76 g (17.25 mmol) of sodium periodate (NaIO$_4$), and then stirred for 5 minutes. Next, about 3 mg of ruthenium chloride, as a catalyst, was added thereto, followed by stirring for two days. At the end of the reaction, the resulting material was extracted with 20 ml of diethyl ether. Following this, a water layer was acidified with 1H HCl, and then extracted with methylene chloride, thereby obtaining 317 mg (75% yield) of (4S-trans)-4,5-dihydro-2,4-diphenyl-oxazoline-5-carboxylic acid. To the obtained product was added 20 ml of diethyl ether, and then 1.0 ml of diazomethane dropwise. The resulting mixture was concentrated under reduced pressure, thereby to obtain 330 mg of (4S-trans)-4,5-dihydro-2,4-diphenyl-oxazoline-5-carboxylic acid methyl ester.

$^1$H NMR (CDCl$_3$) δ 3.87(s, 3H), 4.93(d, J=6.5 Hz, 1H), 5.46(d, J=6.5 Hz, 1H), 7.31–7.57(m, 8H), 8.09–8.12(m, 2H);

$^{13}$C NMR (CDCL$_3$) δ 53.5, 75.4, 83.9, 127.2, 127.5, 128.8, 129.2, 129.4, 129.6, 132.7, 141.8, 164.7, 171.4

EXAMPLE 22

Synthesis of (4S-trans)-4,5-dihydro-4-benzyl-2-phenyl-oxazoline-5-carboxylic Acid 30 ml of a mixed solution of acetonitrile/carbon tetrachloride/water (1:1:1) was added to 395 mg (1.5 mmol) of (4S-trans)-4,5-dihydro-4-benzyl-2-phenyl-5-vinyl-oxazoline while stirring at room temperature. The mixture was added with 819 mg (9.75 mmol) of sodium bicarbonate and 1.76 g (17.25 mmol) of sodium periodate (NaIO$_4$), and then stirred for 5 minutes. Next, about 3 mg of ruthenium chloride, as a catalyst, was added thereto, followed by stirring for two days. At the end of the reaction, the resulting material was extracted with 20 ml of diethyl ether. Following this, a water layer was acidified with 1H HCl, and then extracted with methylene chloride, thereby obtaining 317 mg (75% yield) of (4S-trans)-4,5-dihydro-4-benzyl-2-phenyl-oxazoline-5-carboxylic acid. To the obtained product was added 20 ml of diethyl ether, and then 1.0 ml of diazomethane dropwise. The resulting mixture was concentrated under reduced pressure, thereby to obtain 330 mg of (4S-trans)-4,5-dihydro-4-benzyl-2-phenyl-oxazoline-5-carboxylic acid methyl ester.

$^1$H NMR (CDCl$_3$) δ 2.89(dd, J=7.1 Hz, 13.9 Hz, 1H), 3.12(dd, J=6.1 Hz, J=13.9 Hz, 1H), 3.62(s, 3H), 4.57(dd, J=6.1 Hz, J=7.1 Hz, 1H), 4.65 (d, J=6.1 Hz, 1H), 7.13–7.43 (m, 8H), 7.88–7.90(m, 2H);

$^{13}$C NMR (CDCL$_3$) δ 41.5, 52.4, 72.7, 79.5, 126.7, 127.0, 128.3, 128.4, 128.5, 129.6, 131.6, 136.6, 163.2, 170.8

EXAMPLE 23

Synthesis of (4S-trans)-4,5-dihydro-4-isobutyl-2-phenyl-oxazoline-5-carboxylic Acid 30 ml of a mixed solution of acetonitrile/carbon tetrachloride/water (1:1:1) was added to 392 mg (1.5 mmol) of (4S-trans)-4,5-dihydro-4-isobutyl-2-phenyl-5-vinyl-oxazoline while stirring at room temperature. The mixture was added with 819 mg (9.75 mmol) of sodium bicarbonate and 1.76 g (17.25 mmol) of sodium periodate (NaIO$_4$), and then stirred for 5 minutes. Next, about 3 mg of ruthenium chloride, as a catalyst, was added thereto, followed by stirring for two days. At the end of the reaction, the resulting material was extracted with 20 ml of diethyl ether. Following this, a water layer was acidified with 1H HCl, and then extracted with methylene chloride, thereby obtaining 286 mg (77% yield) of (4S-trans)-4,5-dihydro-4-isobutyl-2-phenyl-oxazoline-5-carboxylic acid. To the obtained product was added 20 ml of diethyl ether, and then 1.0 ml of diazomethane dropwise. The resulting mixture was concentrated under reduced pressure, thereby to obtain 302 mg of (4S-trans)-4,5-dihydro-4-isobutyl-2-phenyl-oxazoline-5-carboxylic acid methyl ester.

$^1$H NMR (CDCl$_3$) δ 1.00(dd, 6H), 1.51(m, 1H), 1.69(m, 1H), 1.98(m, 1H), 3.80(s, 3H), 4.35(dd, J=6.0 Hz, J=9.9Hz, 1H), 4.66(d, J=6.0 Hz, 1H), 7.39–7.52(m, 8H), 7.96–8.00(m, 2H);

$^{13}$C NMR (CDCL$_3$) δ 22.5, 22.8, 25.0, 45.8, 52.5, 70.5, 81.1, 127.2, 128.4, 128.5, 131.6, 162.5, 171.2

EXAMPLE 24

Synthesis of (4S-trans)-4,5-dihydro-4-cyclohexylmethyl-2-phenyl-oxazoline-5-carboxylic Acid 30 ml of a mixed solution of acetonitrile/carbon tetrachloride/water (1:1:1) was added to 350 mg (1.3 mmol) of (4S-trans)-4,5-dihydro-4-cyclohexylmethyl-2-phenyl-5-vinyl-oxazoline while stirring at room temperature. The mixture was added with 819 mg (9.75 mmol) of sodium bicarbonate and 1.76 g (17.25 mmol) of sodium periodate (NaIO$_4$), and then stirred for 5 minutes. Next, about 3 mg of ruthenium chloride, as a catalyst, was added thereto, followed by stirring for two days. At the end of the reaction, the resulting material was extracted with 20 ml of diethyl ether. Following this, a water layer was acidified with 1H HCl, and then extracted with methylene chloride, thereby obtaining 278 mg (75% yield) of (4S-trans)-4,5-dihydro-4-cyclohexylmethyl-2-phenyl-oxazoline-5-carboxylic acid. To the obtained product was added 20 ml of diethyl ether, and then 1.0 ml of diazomethane dropwise. The resulting mixture was concentrated under reduced pressure, thereby to obtain 290 mg of (4S-trans)-4,5-dihydro-4-cyclohexymethyl-2-phenyl-oxazoline-5-carboxylic acid methyl ester.

$^1$H NMR (CDCl$_3$) δ 0.95–1.05(m, 2H), 1.12–1.34(m, 6H), 1.47–1.84(m, 5H), 3.80(s, 3H), 4.40(dd, J=6.6 Hz, J=6.9 Hz, 1H), 4.64(d, J=6.6 Hz, 1H), 7.39–7.52(m, 3H), 7.96–8.00(m, 2H);

$^{13}$C NMR (CDCL$_3$) δ 26.2, 26.5, 26.6, 33.2, 33.5, 34.3, 44.4, 52.5, 69.9, 81.2, 128.4, 128.5, 131.2, 136.4, 165.2, 171.7

EXAMPLE 25

Synthesis of (4S-trans)-4,5-dihydro-2,4-diphenyl-5-(2-hydroxyethyl)oxazoline

To 249 mg (1.0 mmol) of (4S-trans)-4,5-dihydro-2,4-diphenyl-5-vinyloxazoline was added 10 mg of tetrahydrofuran, followed by 6 ml (3.0 mmol) of 9-borabicyclo[3.3.1]nonane (0.5M in THF). The mixture was then stirred for 8 hours at room temperature. At the end of the reaction, the resulting material was added with 2 ml of ethanol, 0.65 ml of 6N NaOH, and 1.3 ml of H$_2$O$_2$, in sequence, stirred for 30 minutes, and then extracted with 10 ml of ethyl acetate twice. The combined organic layer was washed with 10 ml of brine twice, dried with MgSO$_4$, filtered, and then concentrated under reduced pressure. The concentrate was purified by column chromatography (hexane:ethyl acetate=1:2), thereby obtaining 222 mg (83% yield) of (4S-trans)-4,5-dihydro-2,4-diphenyl-5-(2-hydroxyethyl)oxazoline.

$^1$H NMR (CDCl$_3$) δ 2.05(m, 2H), 3.87(m, 2H), 4.66(m, J=4.9 Hz, J=7.3 Hz, 1H), 4.96(d, J=7.3 Hz, 1H), 7.26–7.52 (m, 8H), 8.02–8.04(m, 2H)

$^{13}$C NMR (CDCL$_3$) δ 38.0, 59.5, 75.8, 85.4, 126.7, 127.6, 127.8, 128.4, 128.5, 128.8, 131.7, 141.9, 163.9

EXAMPLE 26

Synthesis of (4S-trans)-4,5-dihydro-4-benzyl-5-(2-hydroxyethyl)-2-phenyloxazoline To 63 mg (1.0 mmol) of (4S-trans)-4,5-dihydro-4-benzyl-2-phenyl-5-vinyloxazoline was added 10 mg of tetrahydrofuran, followed by 6 ml (3.0 mmol) of 9-borabicyclo[3.3.1]nonane (0.5M in THF). The mixture was then stirred for 8 hours at room temperature. At the end of the reaction, the resulting material was added with 2 ml of ethanol, 0.65 ml of 6N NaOH, and 1.3 ml of H$_2$O$_2$, in sequence, stirred for 30 minutes, and then extracted with 10 ml of ethyl acetate twice. The combined organic layer was washed with 10 ml of brine twice, dried with MgSO$_4$, filtered, and then concentrated under reduced pressure. The concentrate was purified by column chromatography (hexane:ethyl acetate=1:2), thereby obtaining 231 mg (82% yield) of (4S-trans)-4,5-dihydro-4-benzyl-5-(2-hydroxyethyl)-2-phenyloxazoline.

$^1$H NMR (CDCl$_3$) δ 1.52 (m, 1H), 1.83 (m, 1H), 2.71 (dd, J=9.0 Hz, J=13.5 Hz, 1H), 3.26 (dd, J=5.0 Hz, J=13.5 Hz, 1H), 3.63 (m, 2H), 4.18(m, J=5.0 Hz, 6.5 Hz, 9.0 Hz, 1H), 4.55(m, J=6.5Hz), 7.23–7.50(m, 8H), 7.93–7.95(m, 2H)

$^{13}$C NMR (CDCL$_3$) δ 38.7, 42.5, 60.0, 74.1, 82.6, 127.4, 128.5, 128.9, 129.0, 129.1, 130.1, 132.1, 138.3, 163.7

EXAMPLE 27

Synthesis of (4S-trans)-4,5-dihydro-5-(2-hydroxyethyl)-4-isobutyl-2-phenyloxazoline To 229 mg (1.0 mmol) of (4S-trans)-4,5-dihydro-4-isobutyl-2-phenyl-5-vinyloxazoline was added 10 mg of tetrahydrofuran, followed by 6 ml (3.0 mmol) of 9-borabicyclo[3.3.1]nonane (0.5M in THF). The mixture was then stirred for 8 hours at room temperature. At the end of the reaction, the resulting material was added with 2 ml of ethanol, 0.65 ml of 6N NaOH, and 1.3 ml of H$_2$O$_2$, in sequence, stirred for 30 minutes, and then extracted with 10 ml of ethyl acetate twice. The combined organic layer was washed with 10 ml of brine twice, dried with MgSO$_4$, filtered, and then concentrated under reduced pressure. The concentrate was purified by column chromatography (hexane:ethyl acetate=1:1), thereby obtaining 161 mg (65% yield) of (4S-trans)-4,5-dihydro-5-(2-hydroxyethyl)-4-isobutyl-2-phenyloxazoline.

$^1$H NMR (CDCl$_3$) δ 0.98(d, 6H), 1.38(m, 1H), 1.62(m, 1H), 1.90(m, 2H), 1.97(m, 1H), 3.88(m, 2H), 3.95(m, 1H), 4.44(m, 1H), 7.39–7.49(m, 3H), 7.92–7.94(m, 2H)

$^{13}$C NMR (CDCL$_3$) δ 23.4, 23.6, 25.6, 38.8, 46.1, 60.4, 71.1, 83.7, 128.7, 128.9, 129.0, 131.9, 163.0

EXAMPLE 28

Synthesis of (4S-trans)-4,5-dihydro-4-cyclohexylmethyl-5-(2-hydroxyethyl)-2-phenyloxazoline To 269 mg (1.0 mmol) of (4S-trans)-4,5-dihydro-4-cyclohexylmethyl-2-phenyl-5-vinyloxazoline was added 10 mg of tetrahydrofuran, followed by 6 ml (3.0 mmol) of 9-borabicyclo[3.3.1]nonane (0.5M in THF). The mixture was then stirred for 8 hours at room temperature. At the end of the reaction, the resulting material was added with 2 ml of ethanol, 0.65 ml of 6N NaOH, and 1.3 ml of H$_2$O$_2$, in sequence, stirred for 30 minutes, and then extracted with 10 ml of ethyl acetate twice. The combined organic layer was washed with 10 ml of brine twice, dried with MgSO$_4$, filtered, and then concentrated under reduced pressure. The concentrate was purified by column chromatography (hexane:ethyl acetate=2:1), thereby obtaining 210 mg (78% yield) of (4S-trans)-4,5-dihydro-4-cyclohexylmethyl-5-(2-hydroxyethyl)-2-phenyloxazoline.

$^1$H NMR (CDCl$_3$) δ 0.95–1.00(m, 2H), 1.15–1.31(m, 3H), 1.37(m, 1H), 1.54(m, 1H), 1.61(m, 1H), 1.65–1.98(m, 8H), 3.88(m, 2H), 3.98(m, 1H), 4.42(m, 1H), 7.38–7.48(m, 3H), 7.92–7.94(m, 2H)

$^{13}$C NMR (CDCL$_3$) δ 26.9, 27.3, 34.2, 34.3, 35.0, 38.8, 44.8, 60.4, 70.5, 83.8, 128.7, 128.9, 129.0, 131.9, 163.0

EXAMPLE 29

Synthesis of (4S-trans)-4,5-dihydro-2,4-diphenyloxazoline-5-acetic Acid 10 ml of a mixed solution of acetonitrile/carbon tetrachloride/water (1:1:1) was added to 267 mg (1.0 mmol) of (4S-trans)-4,5-dihydro-2,4-diphenyl-5-(2-hydroxyethyl) oxazoline. Then, the mixture was added with 546 mg (6.50 mmol) of sodium bicarbonate and 1.18 g (5.50 mmol) of sodium periodate (NaIO$_4$), followed by stirring for 5 minutes. Next, 33.2 mg of ruthenium chloride, as a catalyst, was added thereto, followed by stirring for 24 hours. At the end of the reaction, the resulting material was extracted with 20 ml of diethyl ether. Following this, a water layer was acidified with 1H HCl, and then extracted with methylene chloride, thereby obtaining 275 mg (97% yield) of (4S-trans)-4,5-dihydro-2,4-diphenyl-oxazoline-5-acetic acid. To the obtained product was added 10 ml of diethyl ether, and then 1.0 ml of diazomethane dropwise. The resulting mixture was concentrated under reduced pressure, thereby to obtain 286 mg of (4S-trans)-4,5-dihydro-2,4-diphenyl-oxazoline-5-acetic acid methyl ester.

$^1$H NMR (CDCl$_3$) δ 2.81(dd, J=5.6 Hz, J=15.8 Hz, 1H), 2.91(dd, J=7.6 Hz, J=15.8 Hz, 1H), 3.73(s, 3H), 4.91(m, J=5.6 Hz, 6.3 Hz, 7.6 Hz, 1H), 5.02(d, J=6.3 Hz, 1H), 7.26–7.54(m, 8H), 8.03–8.05(m, 2H)

$^{13}$C NMR (CDCL$_3$) δ 39.8, 52.0, 75.3, 83.2, 126.7, 127.3, 127.9, 128.4, 128.6, 128.8, 131.7, 141.4, 163.8, 170.2

EXAMPLE 30

Synthesis of (4S-trans)-4,5-dihydro-4-benzyl-2-phenyloxazoline-5-acetic Acid 10 ml of a mixed solution of acetonitrile/carbon tetrachloride/water (1:1:1) was added to 281 mg (1.0 mmol) of (4S-trans)-4,5-dihydro-4-benzyl-5-(2-hydroxyethyl)-2-phenyl-oxazoline. Then, the mixture was added with 546 mg (6.50 mmol) of sodium bicarbonate and 1.18 g (5.50 mmol) of sodium periodate (NaIO$_4$), followed by stirring for 5 minutes. Next, 33.2 mg of ruthenium chloride, as a catalyst, was added thereto, followed by stirring for 24 hours. At the end of the reaction, the resulting material was extracted with 20 ml of diethyl ether. Following this, a water layer was acidified with 1H HCl, and then extracted with methylene chloride, thereby obtaining 289 mg (98% yield) of (4S-trans)-4,5-dihydro-4-benzyl-2-phenyl-oxazoline-5-acetic acid. To the obtained product was added 10 ml of diethyl ether, and then 1.0 ml of diazomethane dropwise. The resulting mixture was concentrated under reduced pressure, thereby to obtain 303 mg (98% yield) of (4S-trans)-4,5-dihydro-4-benzyl-2-phenyloxazoline-5-acetic acid methyl ester.

$^1$H NMR (CDCl$_3$) δ 2.32(dd, J=5.5 Hz, J=16.0 Hz, 1H), 2.62(dd, J=8.0 Hz, J=16.0 Hz, 1H), 2.79(dd, J=8.0 Hz, J=13.5 Hz, 1H), 3.22(dd, J=5.5 Hz, J=13.5 Hz, 1H), 3.63(s, 3H), 4.21(m, J=5.8 Hz, 6.0 Hz, 8.0 Hz, 1H), 4.78(m, J=5.5 Hz, 6.0 Hz, 8.0 Hz, 1H), 7.22–7.50(m, 8H), 7.92–7.94(m, 2H)

$^{13}$C NMR (CDCL$_3$) δ 40.6, 42.2, 52.6, 73.7, 80.4, 127.3, 128.2, 129.0, 129.3, 130.2, 132.2, 138.0, 163.7, 170.9

EXAMPLE 31

Synthesis of (4S-trans)-4,5-dihydro-4-isobutyl-2-phenyloxazoline-5-acetic Acid 10 ml of a mixed solution of acetonitrile/carbon tetrachloride/water (1:1:1) was added to 247 mg (1.0 mmol) of (4S-trans)-4,5-dihydro-4-isobutyl-5-(2-hydroxyethyl)-2-phenyl-oxazoline. Then, the mixture was added with 546 mg (6.50 mmol) of sodium bicarbonate and 1.18 g (5.50 mmol) of sodium periodate (NaIO$_4$), followed by stirring for 5 minutes. Next, 33.2 mg of ruthenium chloride, as a catalyst, was added thereto, followed by stirring for 24 hours. At the end of the reaction, the resulting material was extracted with 20 ml of diethyl ether. Following this, a water layer was acidified with 1H HCl, and then extracted with methylene chloride, thereby obtaining 227 mg (87% yield) of (4S-trans)-4,5-dihydro-4-isobutyl-2-phenyl-oxazoline-5-acetic acid. To the obtained product was added 10 ml of diethyl ether, and then 1.0 ml of diazomethane dropwise. The resulting mixture was concentrated under reduced pressure, thereby obtaining 240 mg of (4S-trans)-4,5-dihydro-4-isobutyl-2-phenyloxazoline-5-acetic acid methyl ester.

$^1$H NMR (CDCl$_3$) δ 0.98(d, 6H), 1.41(m, 1H), 1.60(m, 1H), 1.89(m, 1H), 2.61(dd, J=5.5 Hz, J=16.0 Hz, 1H), 2.77(dd, J=7.5 Hz, 16.0 Hz, 1H), 3.75(s, 3H), 3.98(m, J=5.5 Hz, J=6.0 Hz, J=8.0 Hz, 1H), 4.67(m, J=5.5 Hz, 6.0 Hz, 7.5 Hz, 1H), 7.38–7.48((m, 3H), 7.92–7.94(m, 2H)

$^{13}$C NMR (CDCL$_3$) δ 23.5, 25.6, 28.0, 40.6, 52.7, 70.9, 81.6, 128.5, 129.0, 132.0, 162.9, 171.3

EXAMPLE 32

Synthesis of (4S-trans)-4,5-dihydro-4-cyclohexylmethyl-2-phenyloxazoline-5-acetic Acid 10 ml of a mixed solution of acetonitrile/carbon tetrachloride/water (1:1:1) was added to 287 mg (1.0 mmol) of (4S-trans)-4,5-dihydro-4-cyclohexylmethyl-5-(2-hydroxyethyl)-2-phenyl-oxazoline. Then, the mixture was added with 546 mg (6.50 mmol) of sodium bicarbonate and 1.18 g (5.50 mmol) of sodium periodate (NaIO$_4$), followed by stirring for 5 minutes. Next, 33.2 mg of ruthenium chloride, as a catalyst, was added thereto, followed by stirring for 24 hours. At the end of the reaction, the resulting material was extracted with 20 ml of diethyl ether. Following this, a water layer was acidified with 1H HCl, and then extracted with methylene chloride, thereby obtaining 280 mg (93% yield) of (4S-trans)-4,5-dihydro-4-cyclohexylmethyl-2-phenyloxazoline-5-acetic acid. To the obtained product was added 10 ml of diethyl ether, and then 1.0 ml of diazomethane dropwise. The resulting mixture was concentrated under reduced pressure, thereby to obtain 293 mg of (4S-trans)-4,5-dihydro-4-cyclohexylmethyl-2-phenyloxazoline-5-acetic acid methyl ester.

$^1$H NMR (CDCl$_3$) δ 0.89-0.99(m, 2H), 1.14–1.34(m, 3H), 1.40(m, 1H), 1.55–1.90(m, 7H), 2.60(dd, J=5.5 Hz, J=16.0 Hz, 1H), 2.76(dd, J=8.0 Hz, J=16.0 Hz, 1H), 3.70(s, 3H), 4.00(dd, J=6.0 Hz, 1H), 4.66(dd, J=6.0 Hz, 1H), 7.38–7.47(m, 3H), 7.92–7.93(m, 2H)

$^{13}$C NMR (CDCL$_3$) δ 26.8, 27.2, 33.7, 34.2, 40.6, 44.7, 52.7, 70.2, 81.7, 128.5, 129.0, 132.0, 134.3, 162.9, 171.3

As apparent from the description above, the process for the preparation of the oxazoline compound in accordance with the present invention can be carried out using, as the starting material, α-amino acid, such as alanine, valine, leucine, cystein, cyclohexylglycine, cyclohexylalanine, phenylglycine, p-hydroxyphenylglycine, phenylalanine, or p-hydroxyphenylalanine. Besides this, the process in accordance with the present invention allows only one stereoisomer to be selectively synthesized in the preparation of (2R, 3S)-N-benzoyl-3-phenylisoserine which is a component of a side chain of Taxol, thereby being capable of preparing an efficient Taxol side chain and Taxol in a high purity. Additionally, the oxazoline compound prepared in accordance with the process of the present invention is easily chemically converted to β-amino-α-hydroxy acid or γ-amino-β-hydroxy acid, and therefore can be used for the preparation of a physiologically active substance.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed is:

1. A process for the preparation of an oxazoline compound represented by the following formula (2), comprising the steps of:

subjecting a compound employed as a starting material and represented by the following formula (4) to cyclization using a palladium compound as a catalyst to produce a compound represented by the following formula (3);

oxidizing the compound of the formula (3) using a first oxidizing agent and a solution of 9-borabicyclo[3.3.1] nonane in a tetrahydrofuran solvent; and further oxidizing the compound of the formula (3) using a second oxidizing agent and a mixed solvent of acetonitrile/carbon tetrachloride/water to obtain the oxazoline compound represented by the following formula (2):

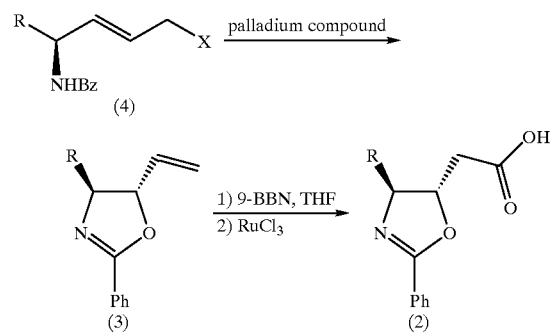

where R is methyl, isopropyl, isobutyl, sec-butyl, thiomethyl, cyclohexyl, cyclohexylmethyl, phenyl, p-hydroxyphenyl, phenylmethyl, or p-hydroxyphenylmethyl, Ph is a phenyl group, X represents leaving group, and is acetate, benzoate, carbonate, or halide, and Bz is a benzoyl group.

2. A process for the preparation of an oxazoline compound according to claim 1, in which the compound of the formula (4) is prepared in accordance with the following reaction scheme using α-amino acid:

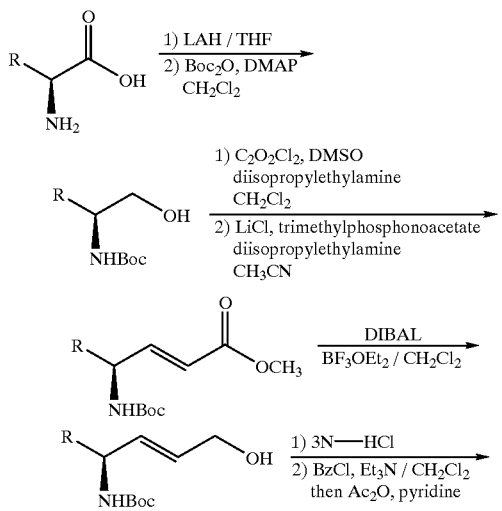

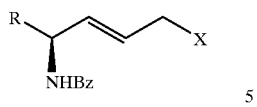

where R is methyl, isopropyl, isobutyl, sec-butyl, thiomethyl, cyclohexyl, cyclohexylmethyl, phenyl, p-hydroxyphenyl, phenylmethyl, or p-hydroxyphenylmethyl, LAH is lithium aluminum hydride (Li(AlH$_4$)), THF is tetrahydrofuran, DMSO is dimethylsulfoxide, DIBAL is diisobutylaluminum hydride, DMAP is dimethylaminopyridine, X represents a leaving group, and is acetate, benzoate, carbonate, or halide, and Bz is a benzoyl group.

3. A process for the preparation of an oxazoline compound according to claim 1, in which the palladium compound is tetrakistriphenylphosphine palladium, a compound having tributyphosphine pallidium, tri-o-tolylphosphine pallidium or tri-p-tolylphosphine pallidium as a ligand, or a combination thereof, or a mixture of triphenylphosphine (Ph$_3$P) with palladium acetate (Pd(OAc)$_2$ or palladium chloride (PdCl$_2$).

4. A process for the preparation of an oxazoline compound according to claim 1, in which the first oxidizing agent is sodium hydroxide (NaOH) or hydrogen peroxide (H$_2$O$_2$), and the second oxidizing agent is sodium hydrogen carbonate (NaHCO$_3$) or sodium periodate (NaIO$_4$).

5. A process for the preparation of an oxazoline compound according to claim 2, in which the α-amino acid is alanine, valine, leucine, cystein, cyclohexylglycine, cyclohexylalanine, phenylglycine, p-hydroxyphenylglycine, phenylalanine, or p-hydroxyphenylalanine.

6. A process for the preparation of an oxazoline compound represented by the following formula (1), comprising the steps of:

subjecting a compound employed as a starting material and represented by the following formula (4) to a cyclization using a palladium compound as a catalyst to produce a compound represented by the following formula (3); and oxidizing the compound of the formula (3) using an oxidizing agent and a mixed solvent of acetonitrile/carbon tetrachloride/water to obtain the oxazoline compound of the formula (1):

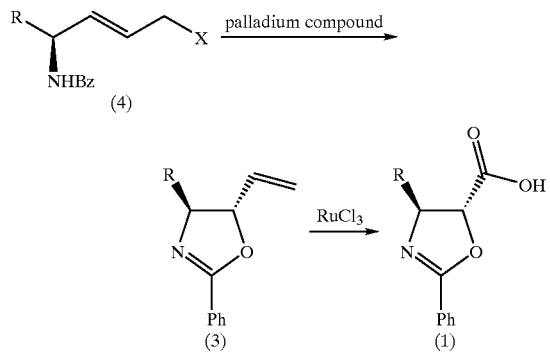

where R is sec-butyl thiomethyl, cyclohexylmethyl, p-hydroxyphenyl, phenylmethyl, or p-hydroxyphenylmethyl, Ph is a phenyl group, X represents leaving group, and is halide, and Bz is a benzoyl group.

* * * * *